(12) United States Patent
Alamaadeed et al.

(10) Patent No.: US 10,138,126 B2
(45) Date of Patent: Nov. 27, 2018

(54) SIMPLE PRODUCTION METHOD FOR GRAPHENE BY MICROORGANISMS

(71) Applicants: Mariam Al Ali Alamaadeed, Doha (QA); Noorunnisa Khanam Patan, Doha (QA)

(72) Inventors: Mariam Al Ali Alamaadeed, Doha (QA); Noorunnisa Khanam Patan, Doha (QA)

(*) Notice: Subject to any disclaimer, the term of this patent is extended or adjusted under 35 U.S.C. 154(b) by 0 days.

(21) Appl. No.: 14/722,015

(22) Filed: May 26, 2015

(65) Prior Publication Data

US 2015/0336799 A1 Nov. 26, 2015
US 2016/0376155 A2 Dec. 29, 2016

Related U.S. Application Data

(60) Provisional application No. 62/002,225, filed on May 23, 2014.

(51) Int. Cl.
*C01B 31/04* (2006.01)
*C12P 3/00* (2006.01)
*C01B 32/192* (2017.01)

(52) U.S. Cl.
CPC ........ *C01B 31/0446* (2013.01); *C01B 32/192* (2017.08); *C12P 3/00* (2013.01)

(58) Field of Classification Search
CPC .................................................. C01B 31/0476
See application file for complete search history.

(56) References Cited

PUBLICATIONS

Salas et a. ACS NANO, 2010, 4(8):4852-4856.*
Akhavan et al. Carbon, 2012, 50:1853-1860.*
Wang et al. Nano Res., 2011, 4(6):563-570.*
Gurunathan et al. International J of Nanomedicine, 2012, 7:5901-5914.*
Noorunnisa Khanam et al. "Biotechnological Production Process and Life Cycle Assessment of Graphene," *Journal of Nanomaterials*, 2017, vol. 2017, Article ID 5671584 (10 pages).
Al-Thani et al. "Graphene Oxide As Antimicrobial Against Two Gram-Positive and Two Gram-Negative Bacteria in Addition to One Fungus," *Online Journal of Biological Sciences*, 2014, vol. 14, No. 3, pp. 230-239.

* cited by examiner

*Primary Examiner* — Bin Shen
(74) *Attorney, Agent, or Firm* — Squire Patton Boggs (US) LLP

(57) ABSTRACT

Systems and methods are provided for producing graphene from graphene oxide in an environmentally friendly, cost effective and simple process, which uses microorganisms as a reducing agent to achieve the desired result. The systems and methods avoid the use of toxic or environmentally harmful reducing agents commonly used as reducing agents in the chemical reduction of GO to obtain graphene.

15 Claims, 25 Drawing Sheets

SIMPLE PRODUCTION METHOD FOR GRAPHENE BY MICROORGANISMS

CROSS REFERENCE TO RELATED APPLICATIONS

This application is related to and claims the benefit and priority of U.S. Provisional Patent Application No. 62/002,225 filed May 23, 2014, which is hereby incorporated herein by reference in its entirety including the references cited therein.

FIELD OF THE INVENTION

The present invention relates to the production of graphene, specifically, to a process for producing graphene from graphene oxide ("GO") with microorganisms acting as a reducing agent.

BACKGROUND OF THE INVENTION

Graphene is a one-atom thick, two-dimensional layer of carbon atoms that are bonded together in a repeating pattern of hexagons. Graphene is strong, flexible, a good conductor for electricity and heat, and has excellent optical properties. Graphene has many industrial uses because of its high surface area, unique physical and chemical properties. For example, Graphene uses, include, but are not limited to solar cells, integrated circuits transistors, transparent screens, camera sensors, DNA sequencing, gas sensing, material strengthening, water desalination, ethanol distillation, antibacterial agents, frequency multiplier, single-molecule gas-detection, quantum dots and energy storage.

Graphene can be produced by different chemical methods, such as mechanical exfoliation, epitaxy, reduction of GO, metal-carbon melts, sodium ethoxide pyrolysis, solvent exfoliation, surfactant-aided exfoliation, interface trapping, and carbon dioxide reduction. Reduction of GO to graphene is one of the methods compatible with large-scale synthesis of graphene. Typically, the chemical reduction of GO to graphene involves the use of reducing agents, such as hydrazine and hydrazine derivatives, which are toxic and release intermediate materials, which may be explosive. The chemical processes for reducing GO to graphene are also very expensive for large-scale processes.

Needs exist for a cost-effective, simple, safe and environmentally friendly process for reducing GO to produce graphene.

SUMMARY OF THE INVENTION

Embodiments of the present invention may include a system and method for aerobically producing graphene from graphene oxide with a microorganism as the reducing agent. The method may include: growing one or more microorganism cultures in suitable media under aerobic conditions; reducing the concentration of the one or more cultures between approximately $10^2$ CFU/mL to approximately $10^{10}$ CFU/mL, where said reduction comprises transferring a portion of the culture to a vessel; immersing a graphene oxide film in the portion of the culture; removing the graphene oxide film from the portion of the cultures after a predetermined time, wherein said removed graphene oxide film contains one or more graphene layers; and recovering the one or more graphene layers.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE INVENTION

Embodiments of the present invention provide improved processes for producing graphene from GO in a simple, safe, environmentally friendly and cost-effective manner. This invention may be practiced over a wide range of processing conditions including, but not limited to the microorganisms used as reducing agents, concentrations of reactants, temperatures, and pressures. The invention may be conducted in the presence or absence of one or more catalysts. The processes as described herein are exemplary processes only and used for illustrative purposes. Other variations and combinations of steps and components may be used as necessary.

Figure 1:
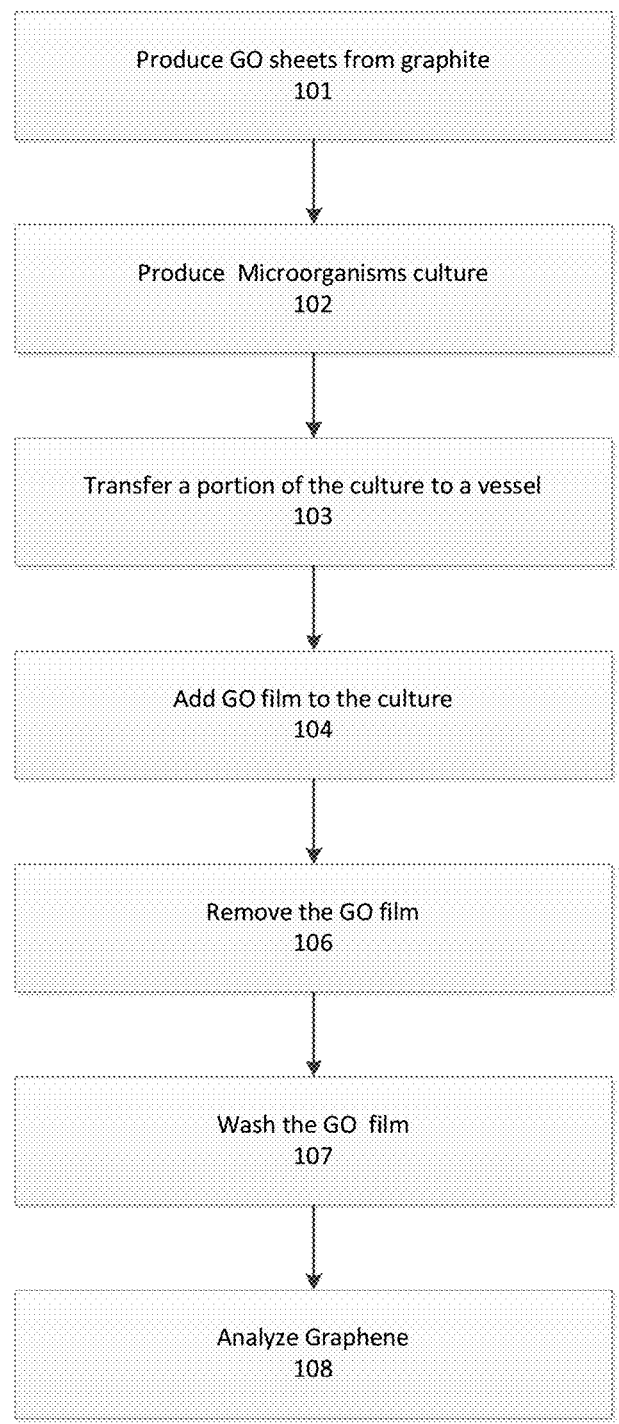
FIG. 1 shows an exemplary process for producing graphene from GO according to one embodiment of the invention.
Figure 2A:
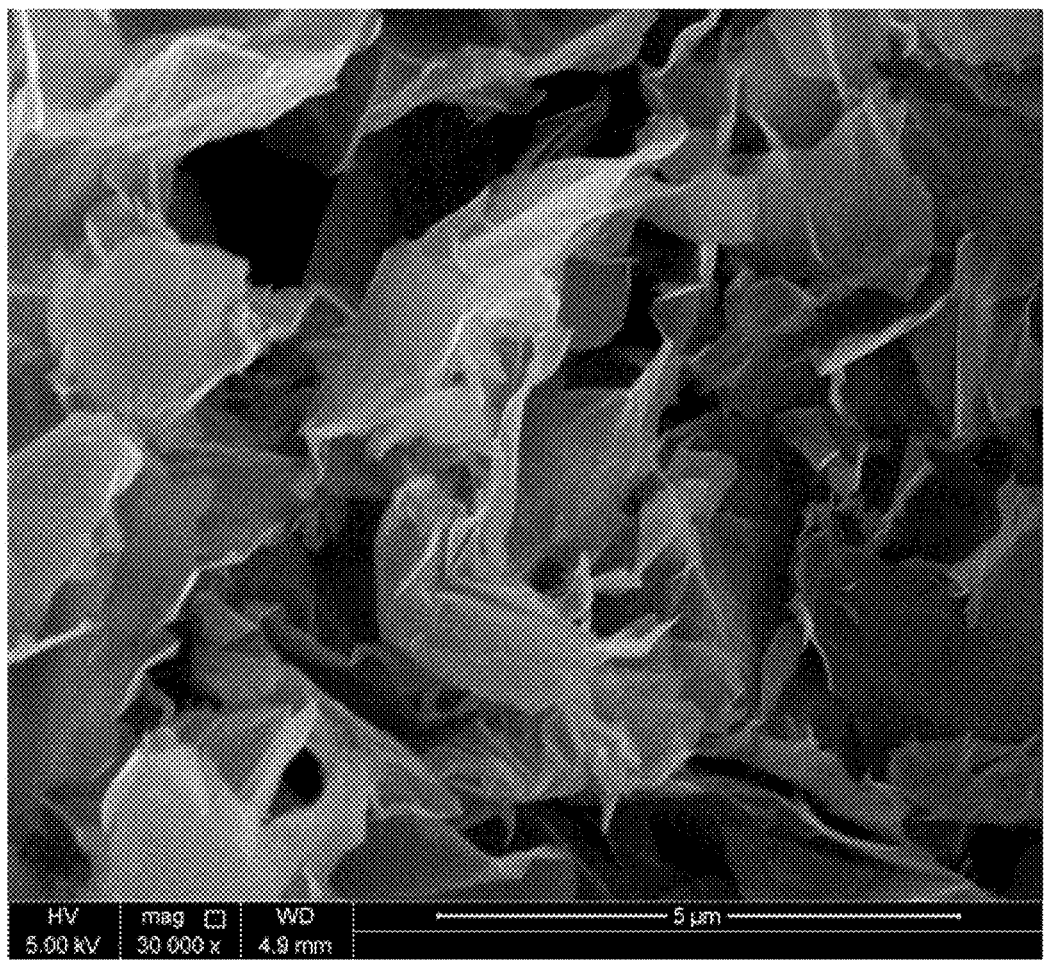
FIGS. 2(A)-(B) are scanning electron microscopy ("SEM") images of graphene produced with *Escherichia coli* according to one embodiment of the invention.
Figure 2B:
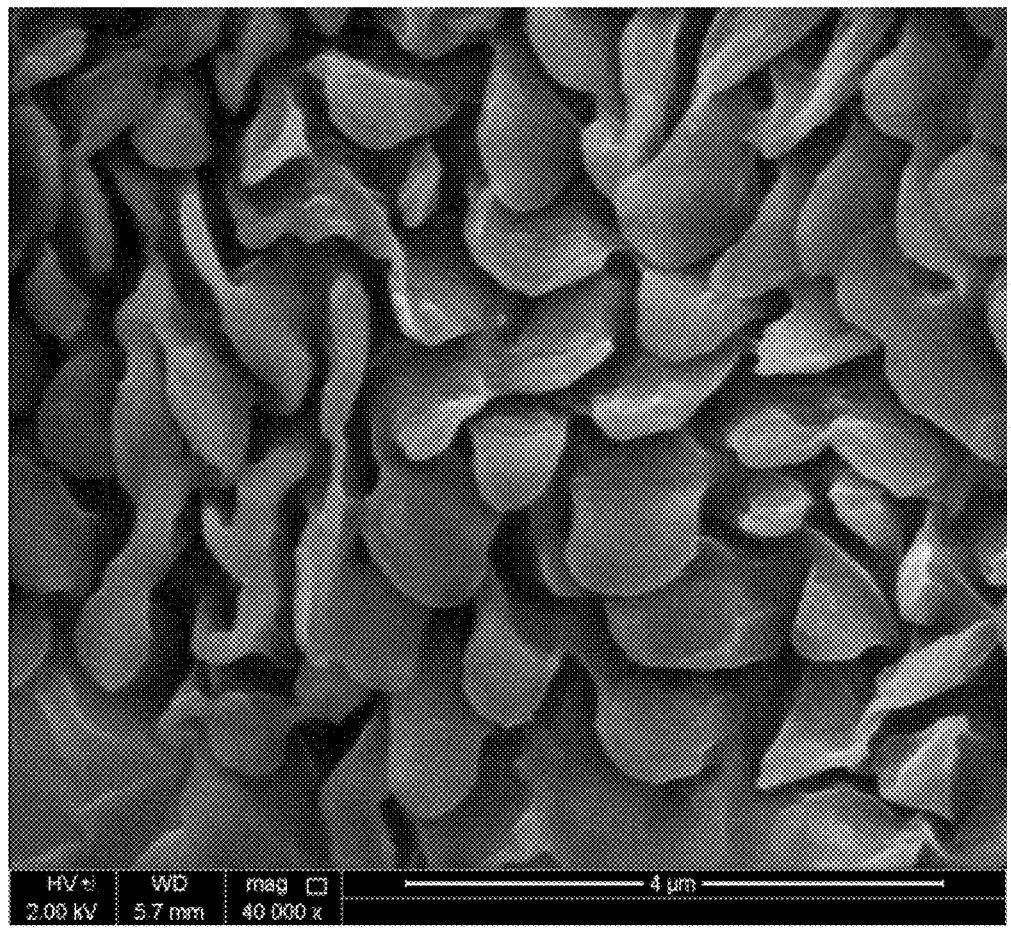
Figure 3A:
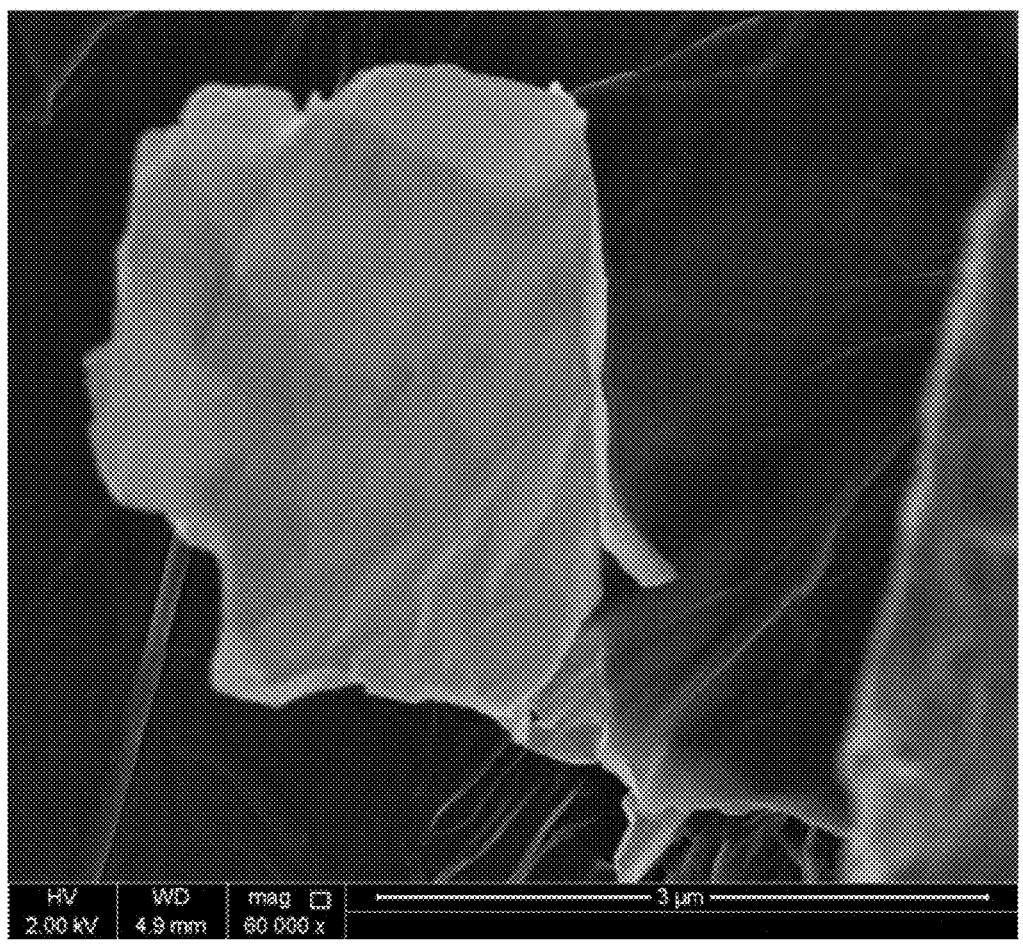
FIGS. 3(A)-(B) are SEM images of graphene produced with *Pseudomonas aeruginosa* according to one embodiment of the invention.
Figure 3B:
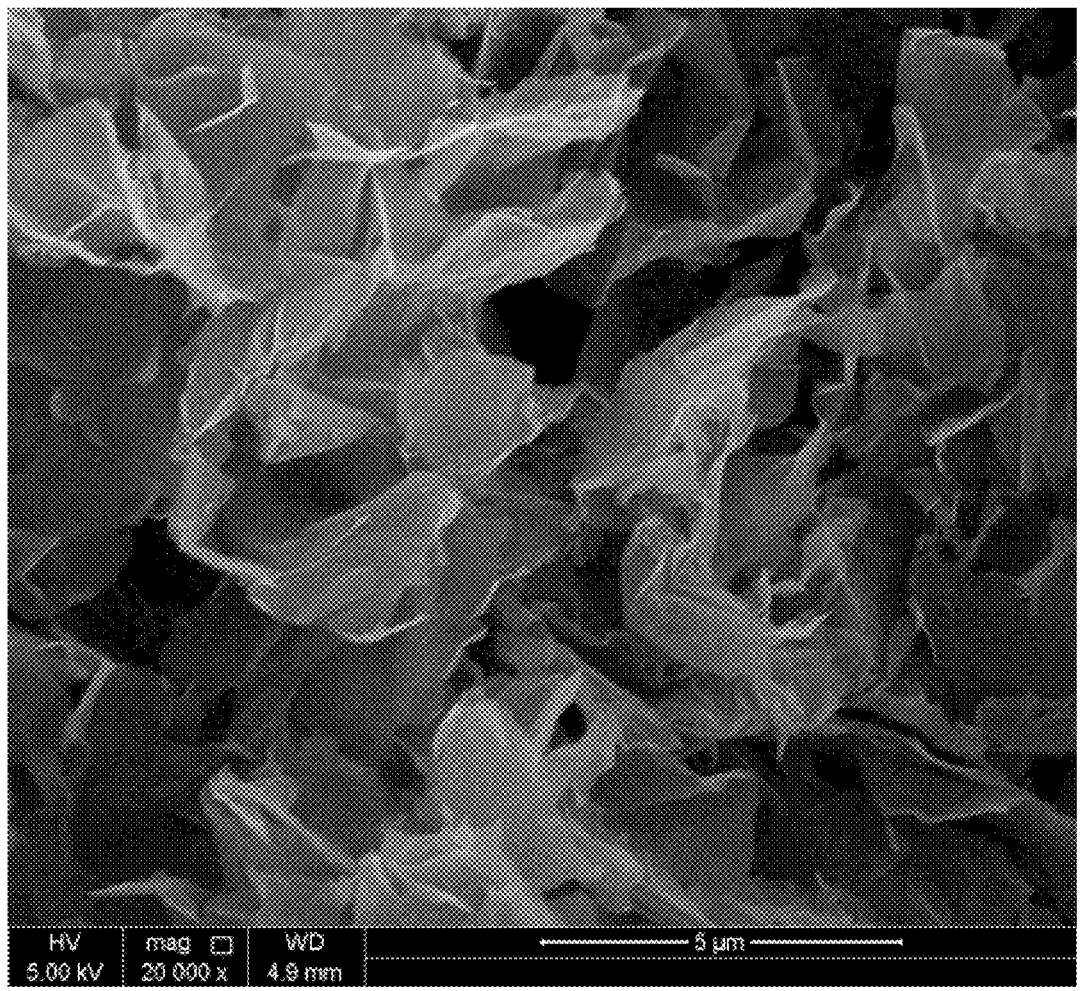
Figure 4A:
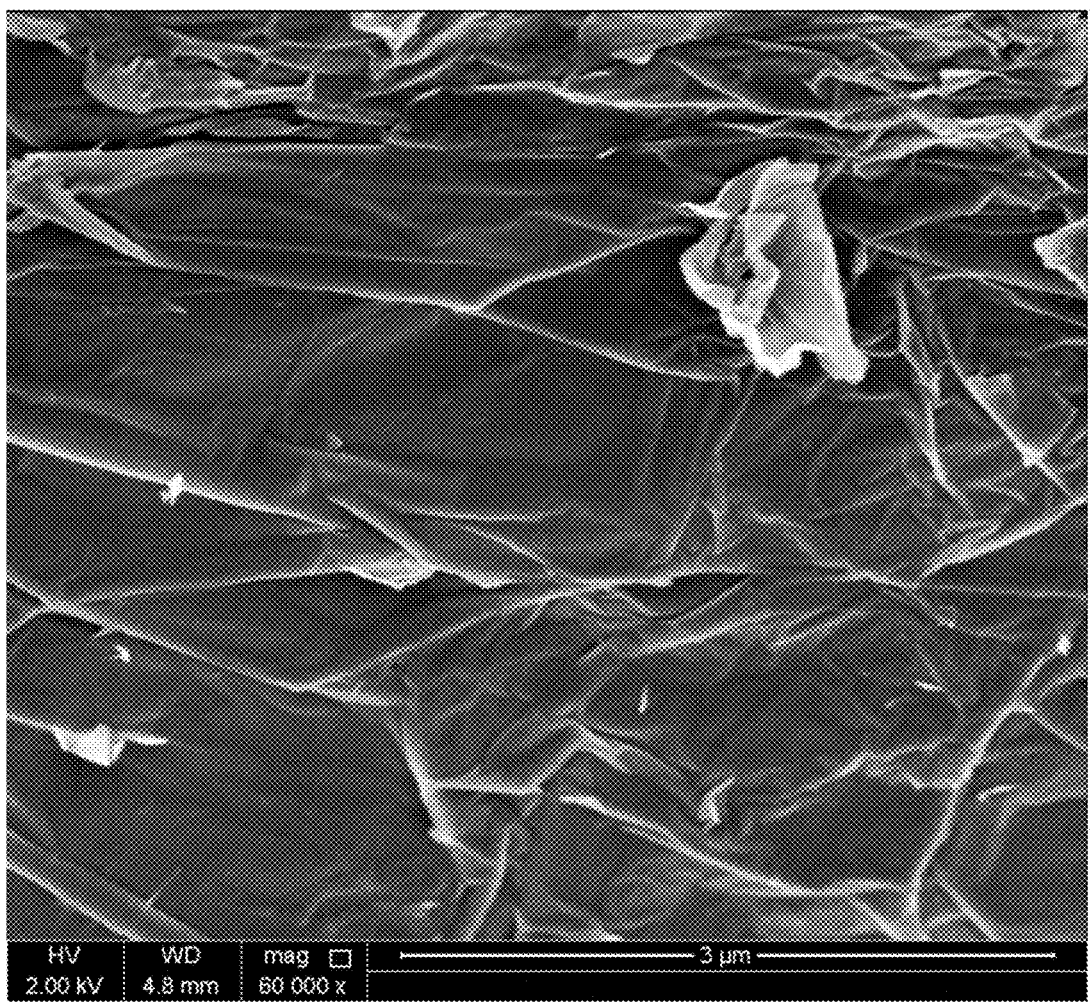
FIGS. 4(A)-(B) are SEM images of graphene produced with *Candida albicans* according to one embodiment of the invention.
Figure 4B:
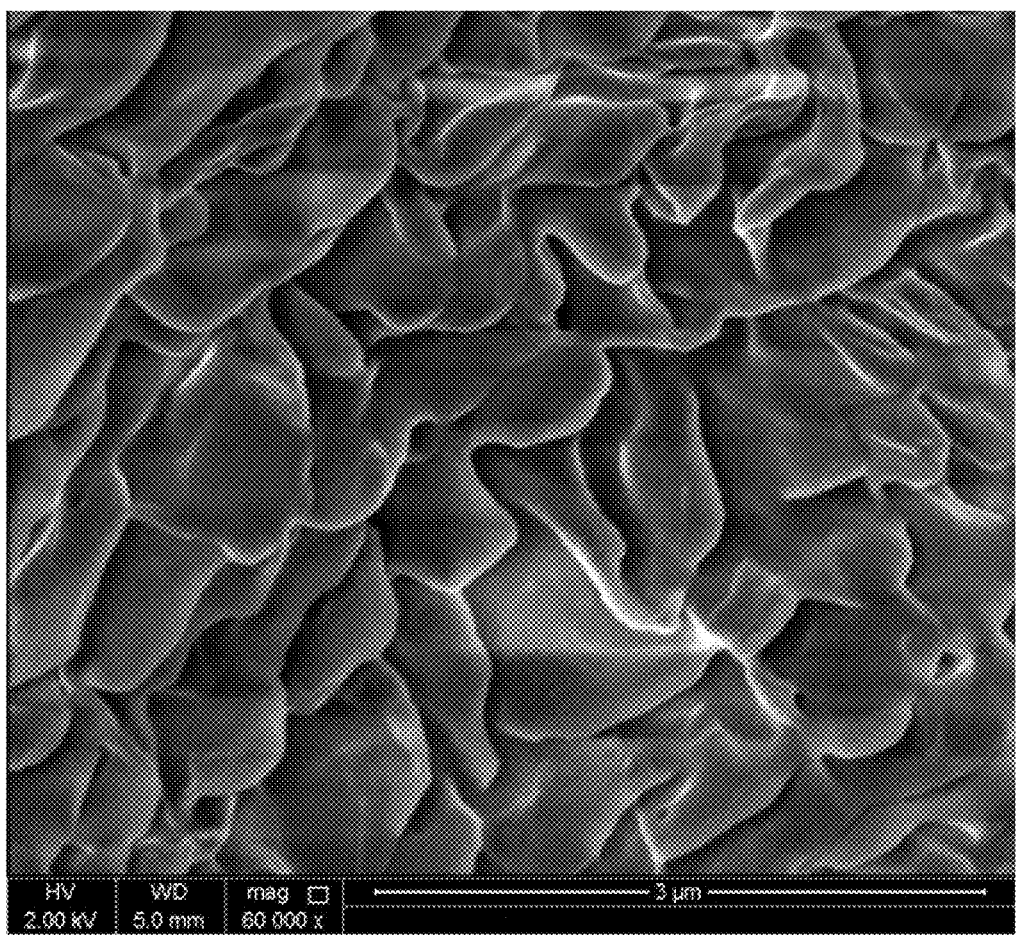
Figure 5A:
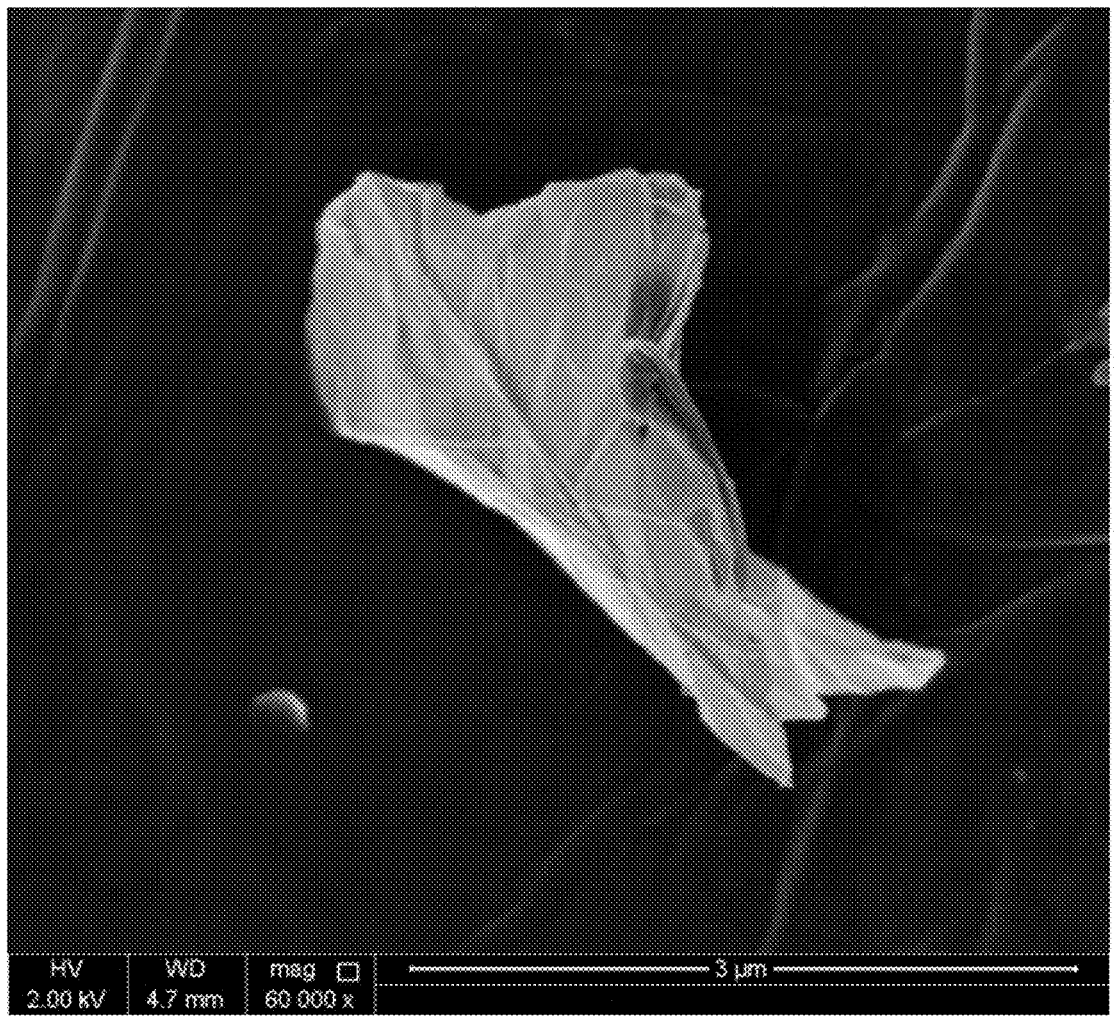
FIGS. 5(A)-(B) are SEM images of graphene produced with *Streptococcus faecalis* according to one embodiment of the invention.
Figure 5B:
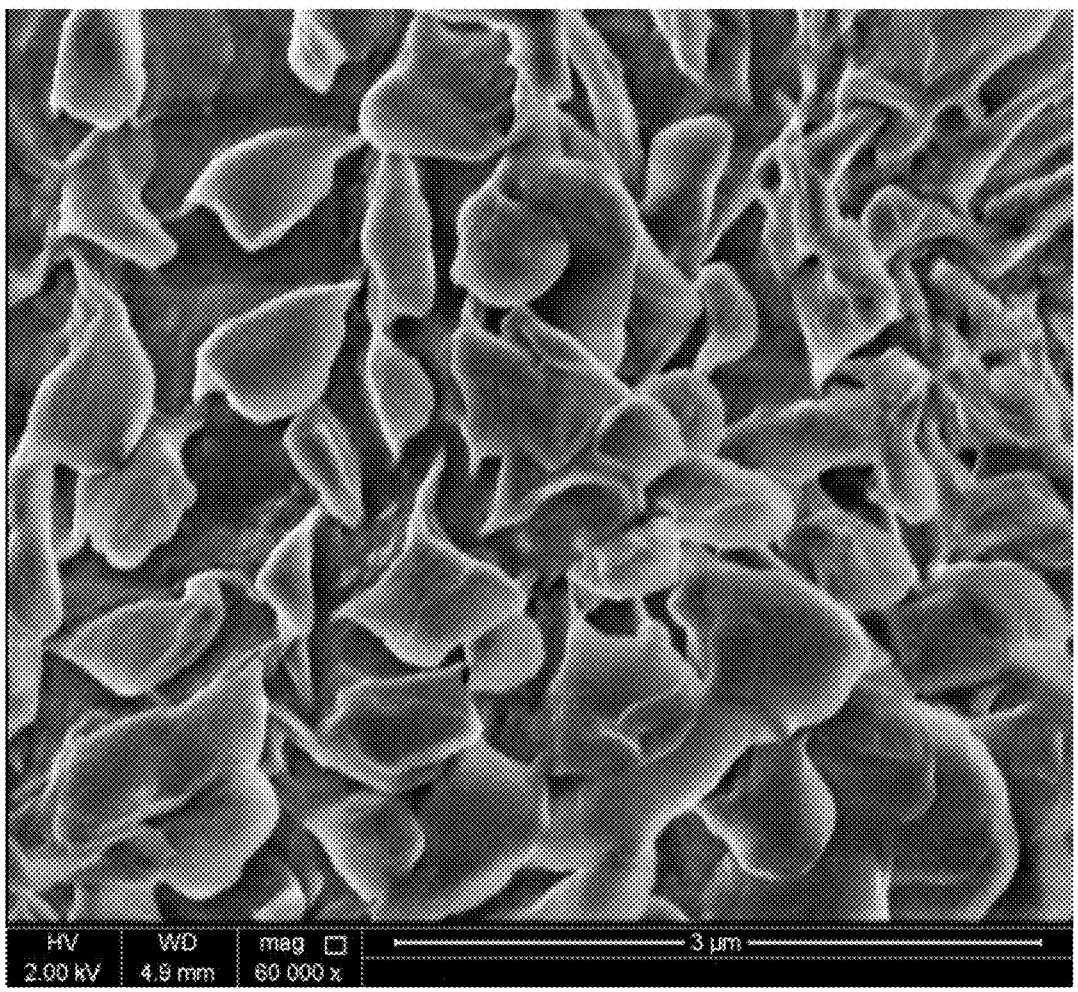
Figure 6A:
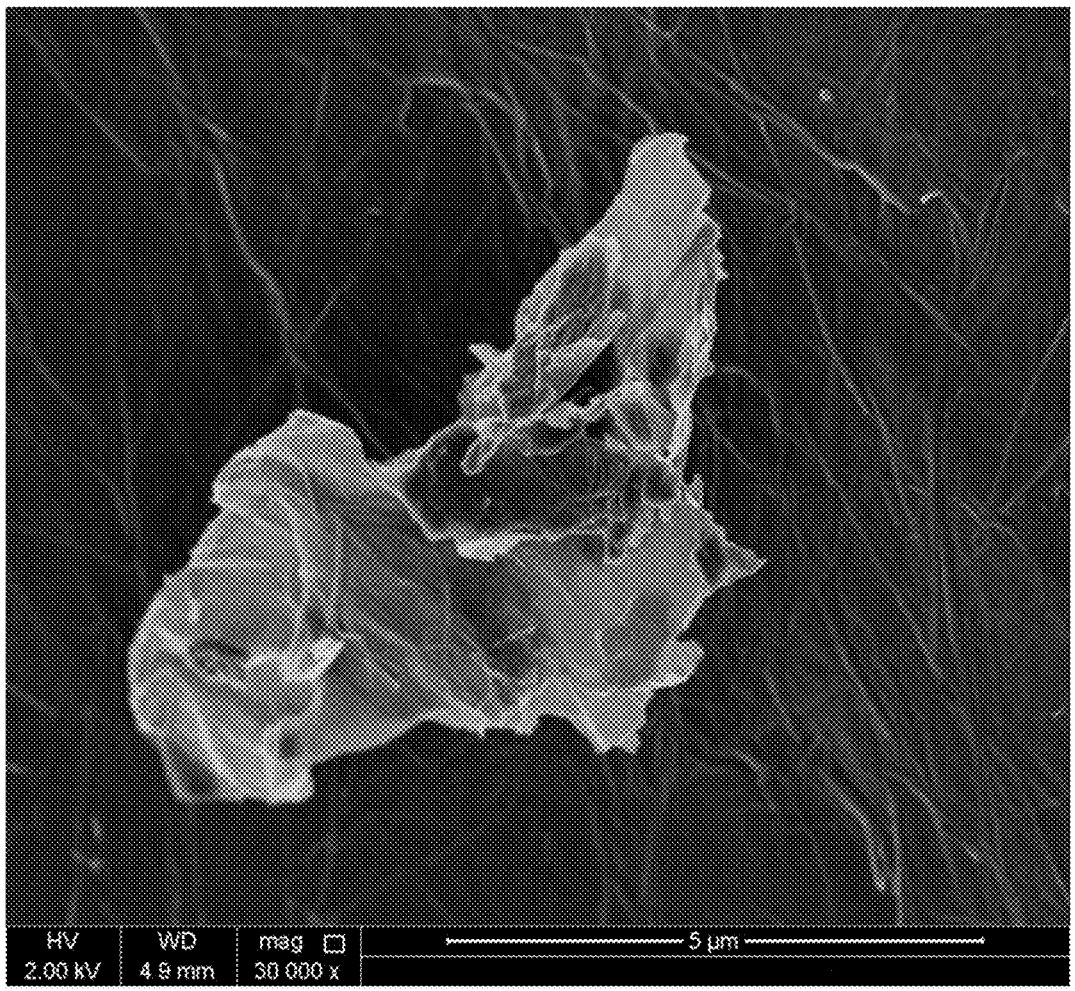
FIGS. 6(A)-(B) are SEM images of graphene produced with *Staphylococcus aureus* according to one embodiment of the invention.
Figure 6B:
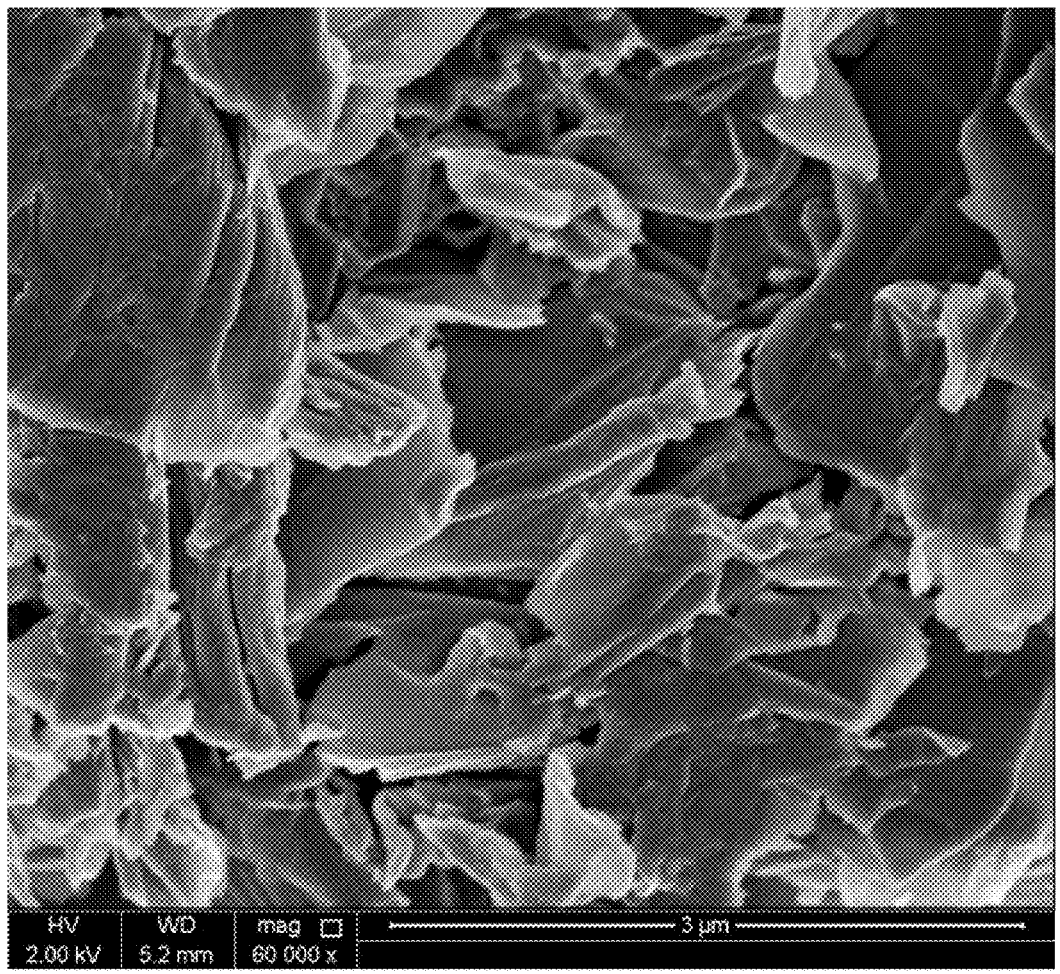

Now referring to FIG. 1, there is shown a process for producing graphene from GO according to one embodiment of the invention. In step 101, GO sheets may be synthesized from natural graphite flakes using any conventional method, such as Hummer's method. In some alternatives, GO sheets may be synthesized from Graphite Powder using any conventional methods. In some alternatives, GO sheets may be synthesized from any conventional materials using any conventional methods. In some alternatives, GO may be synthesized by chemical reduction. In some alternatives, Go may be synthesized by thermal reduction. In some alternatives, plant extracts, green tea, vitamin C, Rose Water and other types of microorganisms may be used in reduction process.

As an example, approximately 3 g of natural graphite flakes may be added to approximately 70 mL of concentrated $H_2SO_4$ under stirring at room temperature. In some alternatives, other conventional acids, such as $HNO_3$ may be used either individually or in combination with other conventional acids. Approximately 1.5 g of $NaNO_3$ may be added to the mixture. The mixture is then cooled to approximately 0° C. Under vigorous agitation, approximately 9 g of $KMnO_4$ is added slowly to the mixture to keep the temperature of the mixture lower than approximately 20° C. The mixture is stirred at approximately 35° C. for approximately two additional hours. Approximately 150 mL of distilled water is added to the mixture. The mixture is stirred at approximately 90° C. for approximately fifteen additional minutes. 500 ml of distilled water is then added to the solution. Approximately 15 mL of 3% $H_2O_2$ is subsequently added slowly to the mixture. The addition of the $H_2O_2$ may result in a change in the color of the mixture, for example, from dark brown to yellow. The mixture may then be filtered and washed with approximately 250 mL of 1:10 HCl aqueous solution to remove metal ions. The mixture may also be washed with approximately 200 mL of distilled water to remove any unreacted acid. The resulting solid or precipitate of GO may be dried in air for approximately for approximately 24 hours, more preferably approximately 12 hours, and most preferably, approximately 8 to approximately 10 hours, or overnight and diluted to make a 0.5% by weight GO aqueous dispersion. In some alternatives, a GO aqueous dispersion may be poured on to a petri plate, cell culture dish and/or other conventional receptacle and dried in air to create a GO film. In some alternatives, the cell culture dish and/or other conventional receptacle and dried in air for approximately 24 hours, more preferably approximately 12 hours, and most preferably, approximately 8 to approximately 10 hours, or overnight.

In Step 102, one or more microorganisms may be grown in suitable medium under aerobic conditions. For example, the microorganism cultures may be incubated for approximately 24 hours in the absence of light at a temperature from approximately 28° C. to approximately 40° C., more preferably approximately 37° C. The microorganism cultures may be incubated in a rotary shaker without any added gas at approximately 80 rpm to approximately 120 rpm, and more preferably, approximately 100 rpm. In some alternatives, the rotary shaker may be operated for approximately several hours to approximately several days. In some alternatives, the microorganisms for the culture may be from stock cultures or substantially biologically pure isolates of the microorganisms. In some alternatives, the microorganisms may include gram positive and gram negative bacteria, grown under aerobic conditions. In some alternatives, the microorganisms may include algae, cyanobacteria, and other types of bacteria and fungus. However, it is understood that other species and/or strains of these microorganisms may be utilized, and suitable alternatives may be selected for their ability to respire and/or grow under aerobic conditions. In some alternatives, the suitable medium may be nutrient broth ("NB"). The NB may include approximately 5 gm/liter of peptic digest of animal tissue, approximately 5 gm/liter of Sodium Chloride, approximately 1.5 gm/liter of beef extract and approximately 1.5 gm/liter of yeast extract. In some alternatives, the suitable medium may be any conventional broth.

In step 103, the culture from step 102, may be diluted to at least $10^4$ CFU/mL, preferably of from $10^2$ to $10^{10}$ CFU/ml, more preferably of from $10^3$ to $10^8$ CFU/ml, and still more preferably, approximately $10^4$ CFU/ml, by transferring a portion of the culture from step 102 to a vessel. In some alternatives, the vessel may be any conventional incubation vessel. In some alternatives, the vessel may be a centrifuge tube. In step 104, approximately 30 mg of GO film from step 101 may be immersed in to the culture under atmosphere conditions [with/without] agitation. In some alternatives, the ratio of the GO film to the culture may be from approximately 0.001% to approximately 0.009%, and most preferably, approximately, 0.003%. The vessel may be in the absence of light and agitated in a rotary shaker without any added gas at approximately 80 rpm to approximately 120 rpm, and more preferably, approximately 100 rpm, under vacuum pressure, and at a temperature from approximately 28° C. to approximately 40° C., and more preferably, approximately 37° C. In some alternatives, the vessel may be maintained at room temperature conditions. At a preset period, for example, after approximately 20 days, in step 106, the GO films may be removed from the vessel. The GO films from step 106 may contain one or more layers of graphene as a result of the microbial reduction discussed above. In step 107, saline solution may be used to wash the GO films. In some alternatives, other conventional solvents may be used to wash the GO films. A yield of approximately 95% of graphene may be recovered from the GO films. In some alternatives, the results of the reduction may be visibly apparent. For example, the color of the GO films may change from brown to black, which may confirm the reduction of the GO. In some alternatives, any conventional techniques may be used to confirm the reduction of the GO.

In step 108, the GO films from step 107, may be analyzed by SEM to confirm the reduction of GO to graphene and the presence of graphene. For example, SEM may be used to study the morphology of the GO films by using a Nova SEM-450. SEM photographs may be taken at different magnifications without gold coating.

Figure 7A:
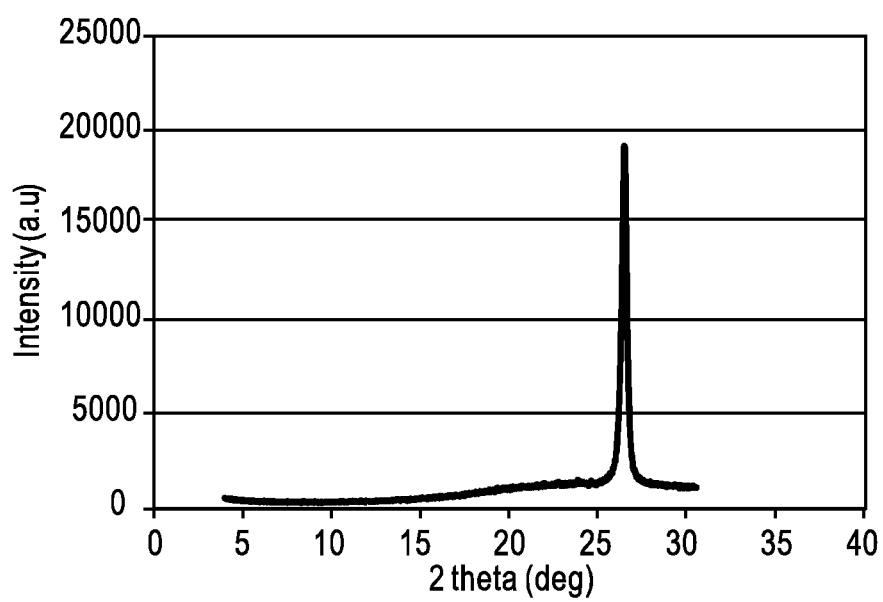
FIG. 7(A) is an X-Ray diffraction ("XRD") graph of graphite.
Figure 7B:
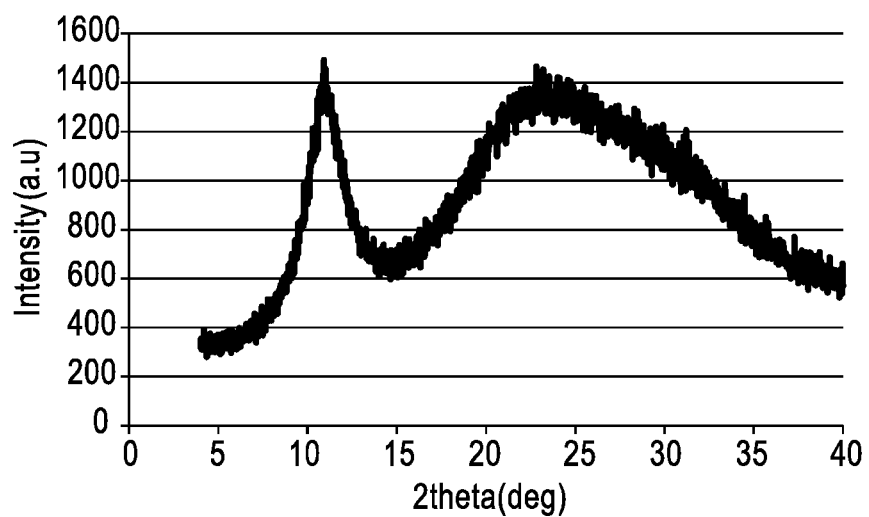
FIG. 7(B) is an XRD graph of graphene oxide.
Figure 8:
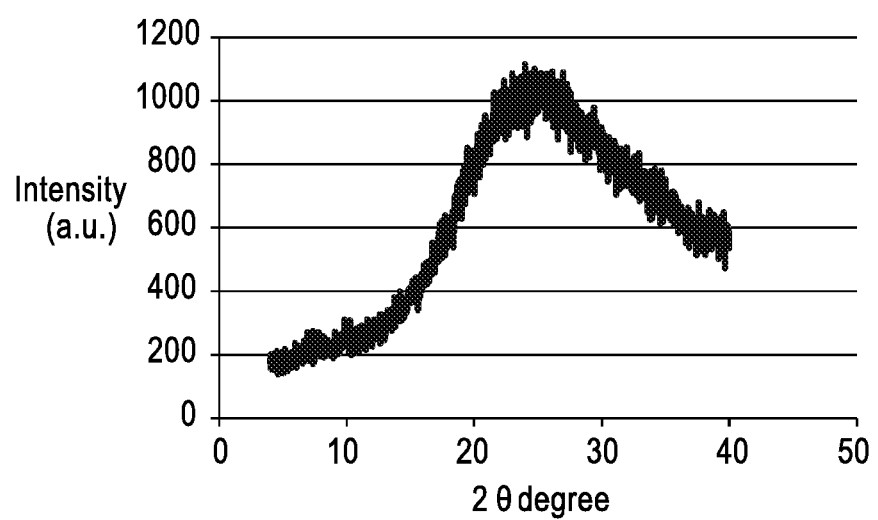
FIG. 8 is an XRD graph of graphene prepared with *Escherichia coli* according to one embodiment of the invention.
Figure 9:
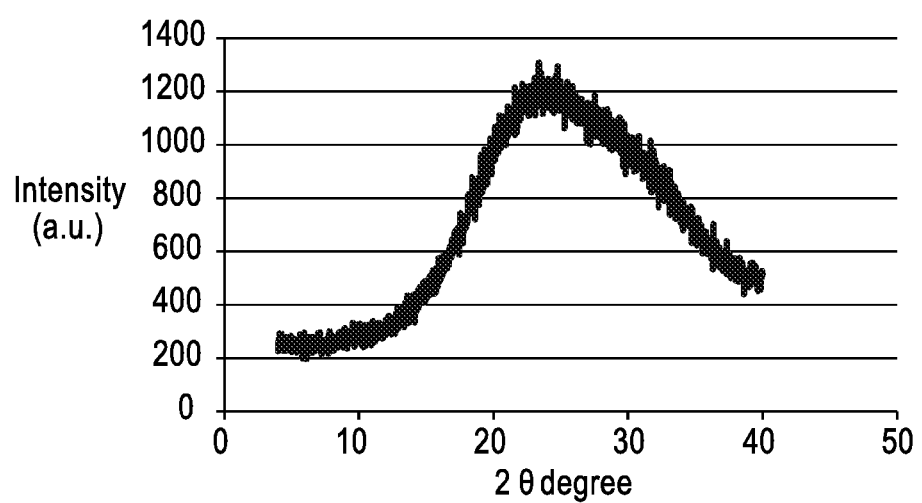
FIG. 9 is an XRD graph of graphene prepared with *Pseudomonas aeruginosa* according to one embodiment of the invention.
Figure 10:
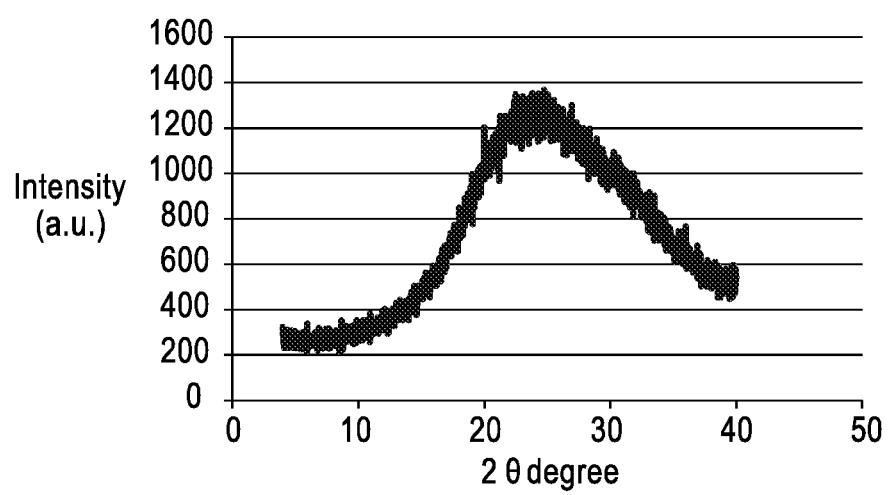
FIG. 10 is an XRD graph of graphene prepared with *Candida albicans* according to one embodiment of the invention.
Figure 11:
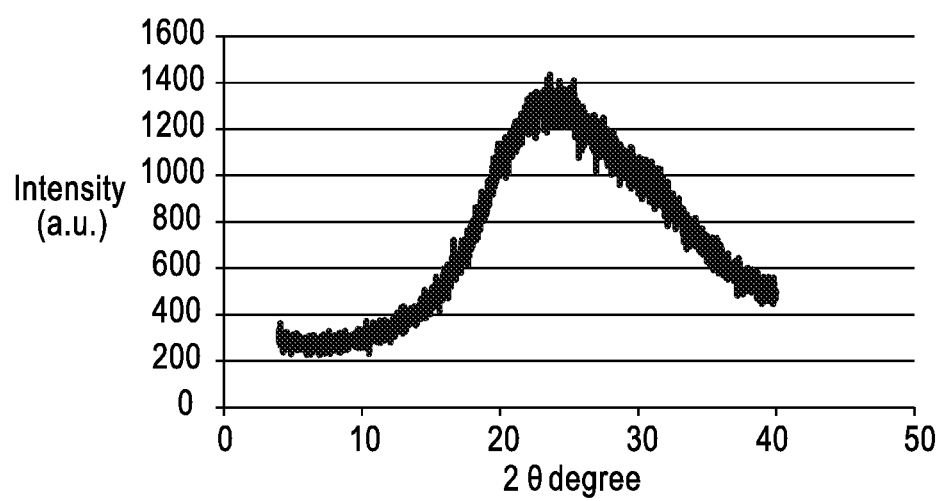
FIG. 11 is an XRD graph of graphene prepared with *Streptococcus faecalis* according to one embodiment of the invention.
Figure 12:
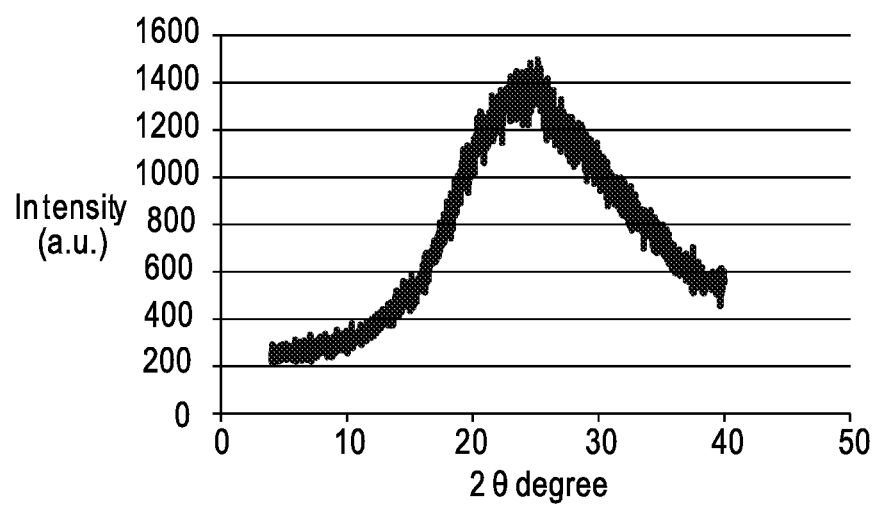
FIG. 12 is an XRD graph of graphene prepared with *Staphylococcus aureus* according to one embodiment of the invention.

Alternatively, in step 108, the GO films from step 107, may be analyzed by Powder XRD, with an X-ray diffractometer to confirm the reduction of GO to graphene and the presence of graphene. For example, a Rigaku MiniFlex2 Desktop X-ray Diffractometer XRD may be used to perform the XRD. FIGS. 7 (a), (b) are XRD graphs of graphite and graphene oxide respectively. Pristine graphite may exhibit basal reflection (002) peaks at 2θ=26.56° (3.3533 A° (0.33533 nm). The diffraction peak of GO may appear at the lower angle from 10.82°, which may correspond to the interlayer spacing of approximately 8.17 A° (0.817 nm). This may show that the oxidation of GO may be significantly larger than that of graphite. The increase in d spacing may be due to the interaction of water molecules and the formation of oxygen containing functional groups between the layers of the graphite. Another peak may appear at 25.92° with interlayer spacing of approximately 3.434 A°. This may be the characteristics peak of hexagonal graphite with d spacing of approximately 0.3434 nm.

Figure 13A:
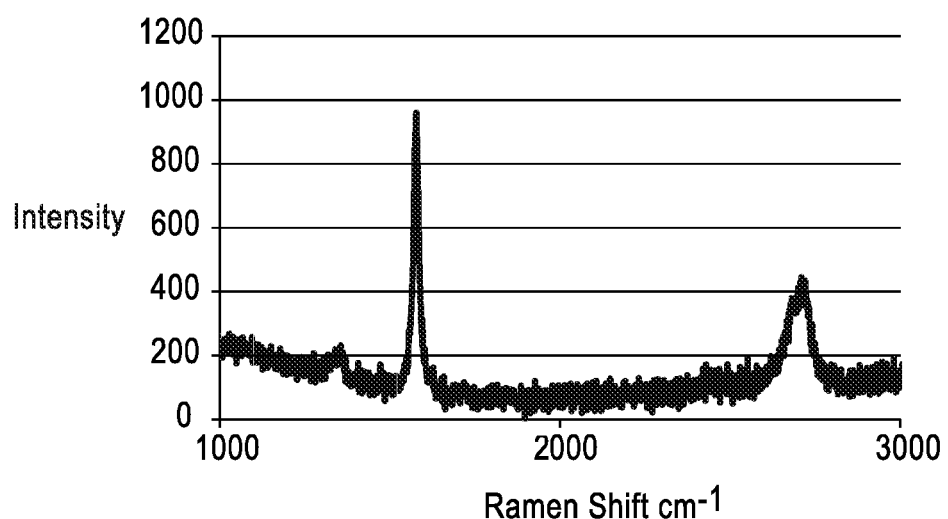
FIG. 13(A) is a Raman Spectroscopy graph of graphite.
Figure 13B:
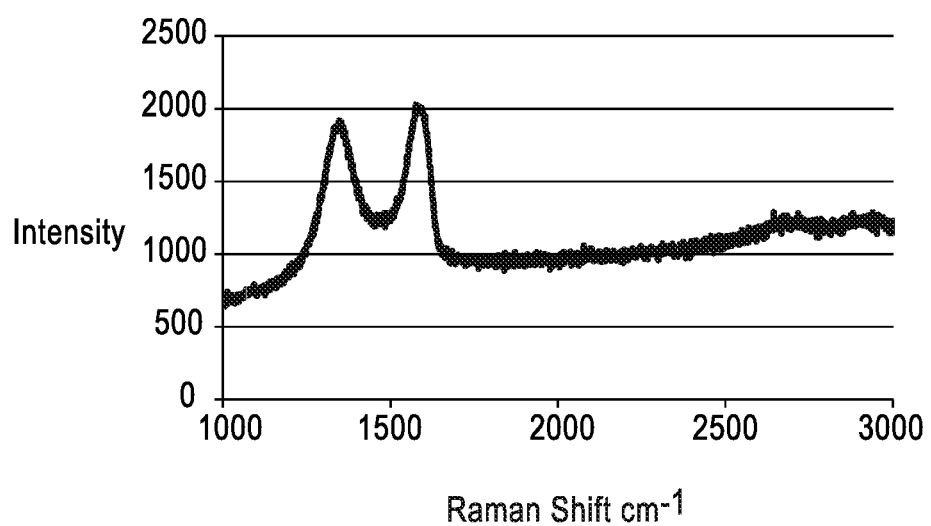
FIG. 13(B) is a Raman Spectroscopy graph of graphene oxide.
Figure 14:
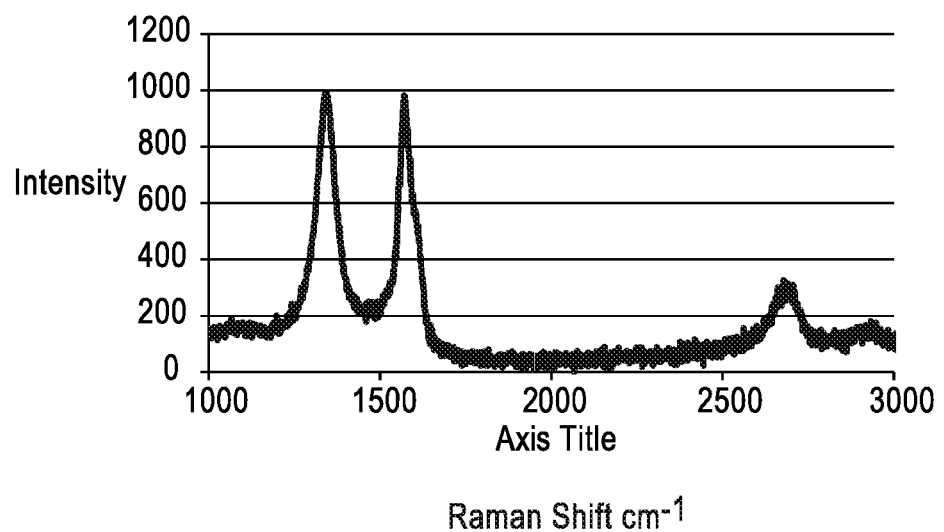
FIG. 14 is a Raman Spectroscopy graph of graphene prepared with *Escherichia coli* according to one embodiment of the invention.
Figure 15:
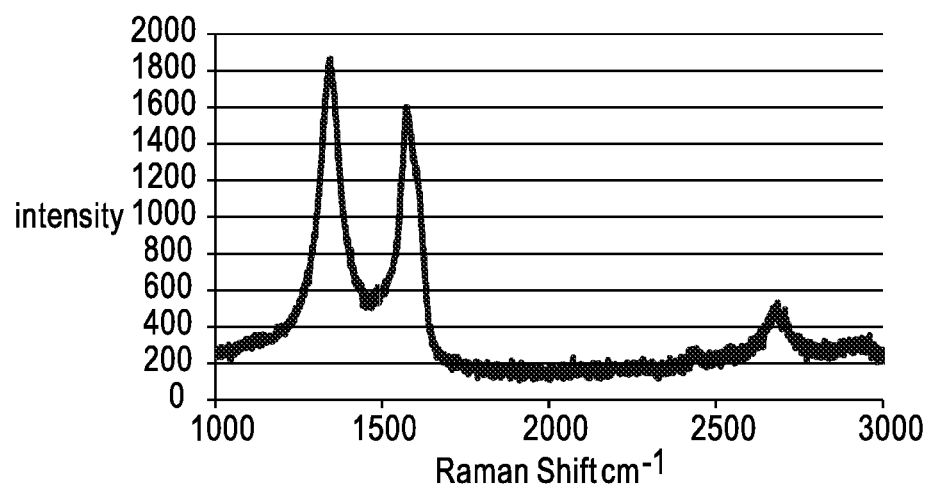
FIG. 15 is a Raman Spectroscopy graph of graphene prepared with *Pseudomonas aeruginosa* according to one embodiment of the invention.
Figure 16:
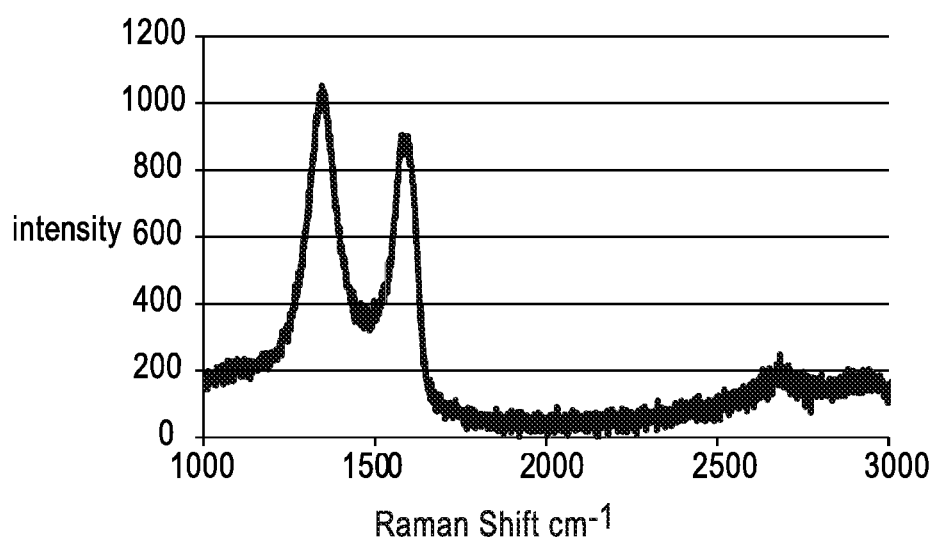
FIG. 16 is a Raman Spectroscopy graph of graphene prepared with *Candida albicans* according to one embodiment of the invention.
Figure 17:
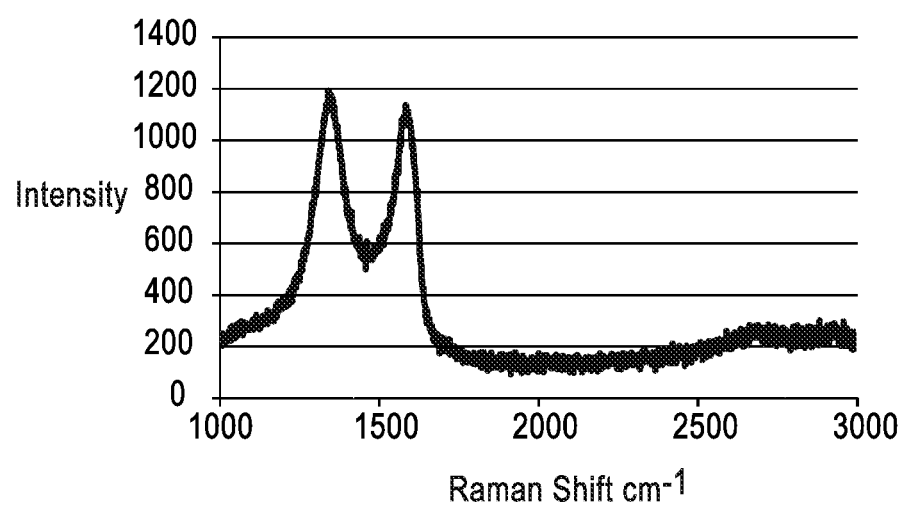
FIG. 17 is a Raman Spectroscopy graph of graphene prepared with *Streptococcus faecalis* according to one embodiment of the invention.
Figure 18:
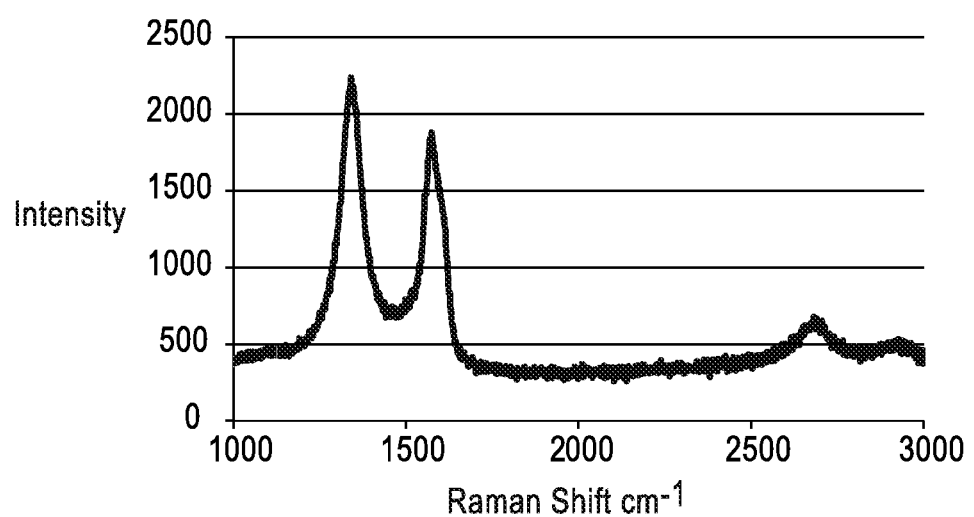
FIG. 18 is a Raman Spectroscopy graph of graphene prepared with *Staphylococcus aureus* according to one embodiment of the invention.

Alternatively, in step 108, the GO films from step 107, may be analyzed Raman spectroscopy to confirm the reduction of GO to graphene and the presence of graphene. Raman spectroscopy may be used to study the ordered or disordered crystal structures of carbonaceous materials, such as graphene. Raman spectroscopy of graphene may be used to study two main features in graphene, the G-Peak (around 1575 cm-1) and D-peak (around 1350 cm-1). These two main features may be assigned to the graphitized structure and local defects or disorders particularly located at the edges of graphene and graphite platelets, respectively. FIGS. 13(a), (b) are graphs of a Raman spectra of graphite and graphene oxide, respectively. The significant structural changes occurring during the chemical processing of pristine graphite to GO, and subsequently to the reduced GO by using microorganisms may also be reflected in their Raman spectra. Raman spectra may be recorded on an In Via Raman micro spectrometer working under macro conditions (f=3 cm) with different excitation lines (532 nm, 633 nm and 785 nm). The samples may be measured directly (without any pre-treatment) and the laser power at the sample may be approximately 2 mW. The presented spectra may be obtained as an average spectrum of approximately 5 different registrations of the Raman spectrum for the same sample. The parameters for each registration may include: spectral range—100-3500 cm-1; number of accumulation—3; and exposure time—10 s. The Raman spectrum of the pristine graphite, may display prominent G peak as the only feature at approximately 1577 cm-1, corresponding to the first-order scattering of the E2 g mode. In the Raman spectrum of GO, the G band may be broadened and shifted to approximately 1604 cm-1. In addition, the D band at approximately 1364 cm-1 may become prominent, indicating the reduction in size of the in-plane sp2 domains, which may possibly be due to the extensive oxidation.

The invention will be illustrated in more detail with reference to the following examples, but it should be understood that the present invention is not deemed to be limited thereto.

Example 1

Each of the microorganisms listed in Table 1 below may be cultured in NB and incubated at approximately 30° C. for approximately 24 hours in the absence of light. The culture may be diluted to approximately $10^4$ CFU/mL by transferring approximately 10 μl of each organism to an incubation vessel. Approximately 30 mg of GO film may be immersed in the culture. The vessel may be in the absence of light and agitated in a rotary shaker without any added gas at approximately 100 rpm, under vacuum pressure, and at a temperature of approximately 37° C. After approximately 20 days, the GO film, which contains one or more graphene layers may be removed from the culture and washed with saline. A yield of approximately 95% of graphene may be recovered from the GO film. The color of the GO film may change from brown to black, when the reduction of the GO is complete. The GO film may be analyzed with SEM, XRD, and Raman spectroscopy to confirm the presence of graphene.

TABLE 1

| Microorganism | Collection No. |
| --- | --- |
| Escherichia coli | A.T.C.C. 41570 |
| Pseudomonas aeruginosa | A.T.C.C. 25619 |
| Candida albicans | A.T.C.C. 10231 |
| Streptococcus faecalis | A.T.C.C. 19433 |
| Staphylococcus aureus | A.T.C.C. 11632 |

SEM images of reduced GO films by the microorganisms in Table 1 may be smooth with folded shapes at the edges, which may look like waves as illustrated in FIGS. 2-6. SEM images may appear to be crumpled and wrinkled structures as illustrated in in FIGS. 2-6. SEM images may be aggregated, thin, crumpled sheets closely associated with each other and forming a disordered solid as illustrated in in FIGS. 2-6. The geometric wrinkling arising from π-π interaction within sheets of graphene may not only minimize the surface energy but may also induce mechanical integrity with tensile strength and good film-forming ability.

After reduction of GO with microorganisms from Table 1 above, the peak at approximately 10.82° disappears and may be replaced with a broad peak appears, starting from approximately 22° to approximately 24° as illustrated in FIGS. 8-12. The interlayer spacing may decrease, which suggests that removal of oxygen and water from the interlayer during exfoliation may occur to a large extent. This peak may also shows a loss of the long range order in graphene. The disappearance of graphene oxide peak and appearance of a broad band from 2θ=approximately 22° to approximately 24° in FIGS. 8-12 may indicate that the GO may have been reduced and that a few layers of graphene may have been formed.

The Raman spectrum of the reduced GO ° as illustrated in FIGS. 14-18 may also contain both G and D bands at approximately 1584 cm-1 and approximately 1356 cm-1, respectively. The D/G intensity ratio compared to that in GO may be increased. This change may suggest a decrease in the average size of the sp2 domains upon reduction of the exfoliated GO, and can be explained if new graphitic domains may have been created that may be smaller in size to the ones present in GO before the reduction, but more numerous in number. The $_{ID/IG}$ ratio of the GO sheets may have decreased after reduction by microorganisms.

The above results from Example 1 suggest that the microorganisms in Table 1 above may reduce GO to graphene and one or more layers of graphene may have been formed.

Although the foregoing description is directed to the preferred embodiments of the invention, it is noted that other variation and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. A method of aerobically producing graphene from graphene oxide with a microorganism comprising:
   a) growing one or more microorganism cultures in suitable media under aerobic conditions;
   b) reducing concentration of the one or more cultures between approximately $10^2$ CFU/mL to approximately $10^{10}$ CFU/mL, wherein said reduced concentration comprises transferring a portion of the culture to a vessel;
   c) adding graphene oxide to the vessel under atmospheric conditions;
   d) removing the added graphene oxide from the vessel after a predetermined time, wherein said removed graphene oxide contains graphene; and
   e) washing the removed graphene oxide with a solution and recovering the graphene, wherein the yield of recovered graphene is greater than 50% of the added graphene oxide;
   wherein the one or more microorganism cultures is selected from the group consisting of: *Pseudomonas aeruginosa, Candida albicans, Streptococcus faecalis, Staphylococcus aureus*, algae, cyanobacteria, and combinations thereof,
   wherein the microorganism reduces graphene oxide to graphene.

2. The method of claim 1, wherein the suitable media is nutrient broth.

3. The method of claim 2, wherein the nutrient broth comprises approximately 5 gm/liter of peptic digest of animal tissue, approximately 5 gm/liter of sodium chloride, approximately 1.5 gm/liter of beef extract and approximately 1.5 gm/liter of yeast extract.

4. The method of claim 1, wherein the portion is approximately 10 µl.

5. The method of claim 1, wherein the graphene oxide is a film of graphene oxide at a concentration of approximately 30 mg per $10^4$ CFU/mL of the one or more cultures.

6. The method of claim 1, wherein the aerobic conditions comprise a period of 24 hours, a temperature from approximately 25° C. to approximately 40° C., absence of light or a shaker without any additional gas.

7. The method of claim 6, wherein the temperature is approximately 37° C.

8. The method of claim 1, wherein the concentration of the one or more cultures is approximately $10^4$ CFU/mL.

9. The method of claim 1, wherein the yield of recovered graphene is greater than 70% of the added graphene oxide.

10. The method of claim 1, wherein the yield of recovered graphene is greater than 80% of the added graphene oxide.

11. The method of claim 1, wherein the yield of recovered graphene is greater than 90% of the added graphene oxide.

12. The method of claim 1, where the solution in step e) comprises saline.

13. The method of claim 1, wherein the graphene oxide is added in the absence of light.

14. The method of claim 1, wherein the predetermined time is approximately 2-20 days.

15. The method of claim 1, wherein the predetermined time is approximately 20 days.

* * * * *